(12) United States Patent
Yanagidaira et al.

(10) Patent No.: US 7,134,997 B2
(45) Date of Patent: Nov. 14, 2006

(54) BIOLOGICAL INFORMATION DETECTION APPARATUS

(75) Inventors: Masatoshi Yanagidaira, Tsurugashima (JP); Mitsuo Yasushi, Tsurugashima (JP)

(73) Assignee: Pioneer Corporation, Tokyo-to (JP)

( * ) Notice: Subject to any disclaimer, the term of this patent is extended or adjusted under 35 U.S.C. 154(b) by 409 days.

(21) Appl. No.: 10/842,475

(22) Filed: May 11, 2004

(65) Prior Publication Data

US 2004/0230104 A1    Nov. 18, 2004

(30) Foreign Application Priority Data

May 12, 2003    (JP)    ............................ P2003-132743

(51) Int. Cl.
 *A61B 5/04*    (2006.01)
 *A61B 5/02*    (2006.01)
 *G08B 23/00*   (2006.01)
(52) U.S. Cl. ...................... 600/300; 600/519; 600/483; 340/575
(58) Field of Classification Search ................ 600/300, 600/509, 519, 520, 483, 484, 500, 502, 504, 600/503, 506, 544, 547, 549; 340/575, 576
See application file for complete search history.

(56) References Cited

U.S. PATENT DOCUMENTS 4,706,072 A * 11/1987 Ikeyama ..................... 340/576
5,574,641 A    11/1996 Kawakami et al.
6,104,296 A * 8/2000 Yasushi et al. ............. 340/576
6,312,382 B1 * 11/2001 Mucci et al. ............... 600/437
7,088,250 B1 * 8/2006 Yasushi ..................... 340/573.1

FOREIGN PATENT DOCUMENTS

| EP | 1 291 226 A2 | 3/2003 |
|---|---|---|
| EP | 1 304 250 A2 | 4/2003 |
| JP | 6-255518 | 9/1994 |
| JP | 06255518 | 9/1994 |

\* cited by examiner

*Primary Examiner*—Kennedy Schaetzle
(74) *Attorney, Agent, or Firm*—Nixon & Vanderhye P.C.

(57) ABSTRACT

While detecting a missing section from a biological signal acquired from a human body and while storing the biological signal values obtained at n (where n is a natural number) consecutive points in time, weighted addition is conducted on the biological signal values obtained at n points in time. In outputting its result as a final biological signal, the biological signal value at each of points in time included in the missing section is changed to an average value of the biological signal values at points in time which are not in the missing section.

4 Claims, 4 Drawing Sheets

FIG. 3

| HEART RATE DATA | EFFECTIVE DATA FLAG |
|---|---|
| X(1) | FL |
| X(2) | |
| X(3) | |
| X(4) | |
| X(5) | FL |
| X(6) | FL |
| ⋮ | ⋮ |
| X(n−2) | FL |
| X(n−1) | FL |
| X(n) | FL |

BIOLOGICAL INFORMATION DETECTION APPARATUS

BACKGROUND OF THE INVENTION

1. Field of the Invention

The present invention relates to a biological information detection apparatus which detects biological information of a human being or an animal.

2. Related Art

At the present time, there has been proposed a sleepiness alarm system which judges the sleepiness state of a driver who is driving a vehicle by measuring a biological information such as heart rate, pulsebeat, respiration, temperature, skin resistance and blood pressure of the driver and notifies the driver of the sleepiness state. Electrodes which detect biological information from hands of the driver are attached to a steering wheel of a vehicle having such a sleepiness alarm system mounted thereon. Therefore, the driver must always touch the electrodes and consequently the driver is forced to undergo an excessive burden. Therefore, even if the driver temporarily releases one hand or both hands from the electrodes, a heart rate detection apparatus capable of correctly detecting the heart rate serving as biological information of the driver has been proposed. See, for example, Japanese Patent Application Laid-Open Publication No. Hei-06-255518. If the driver temporarily releases one hand or both hands from the electrodes attached to the steering wheel and consequently the heart rate signal from the electrodes is missing in such a heart rate detection apparatus, the missing section of the heart rate signal is compensated for by using a heart rate signal obtained after recovery.

If the time over which the driver releases one hand or both hands from the electrodes becomes long in such a heart rate detection apparatus, however, the time when processing is conducted to compensate for the missing section of the heart rate signal is delayed. This results in a problem that the measurement of the heart rate is stopped over this time period.

SUMMARY OF THE INVENTION

In order to solve the problem, the present invention has been achieved. An object of the present invention is to provide a biological information detection apparatus capable of acquiring biological information of a driver continuously even while the driver keeps one hand or both hands apart from electrodes for detecting biological information.

The above object of the present invention can be achieved by a biological information detection apparatus which detects biological information of a human body, provided with: a sensor which detects an electric signal corresponding to the biological information from the human body as a biological signal; a missing detection device which detects a missing section of the biological signal; a storage device which stores the biological signal at each of n (where n is a natural number) consecutive points in time; an average calculation device which calculates an average value of the biological signal at points in time which are included in the n points in time and which are not included in the missing section; a weighted addition device which outputs a result obtained by conducting weighted addition on the biological signal at the n points in time, as a final biological signal; and a missing interpolation device which, in conducting the weighted addition, changes the biological signal at each of the points in time included in the missing section to the average value.

BRIEF DESCRIPTION OF THE DRAWINGS

FIG. 3 is a diagram showing an example of a storage form of an internal memory.

DESCRIPTION OF THE PREFERRED EMBODIMENT

Hereafter, an embodiment of the present invention will be described in detail with reference to the drawings.

Figure 1:
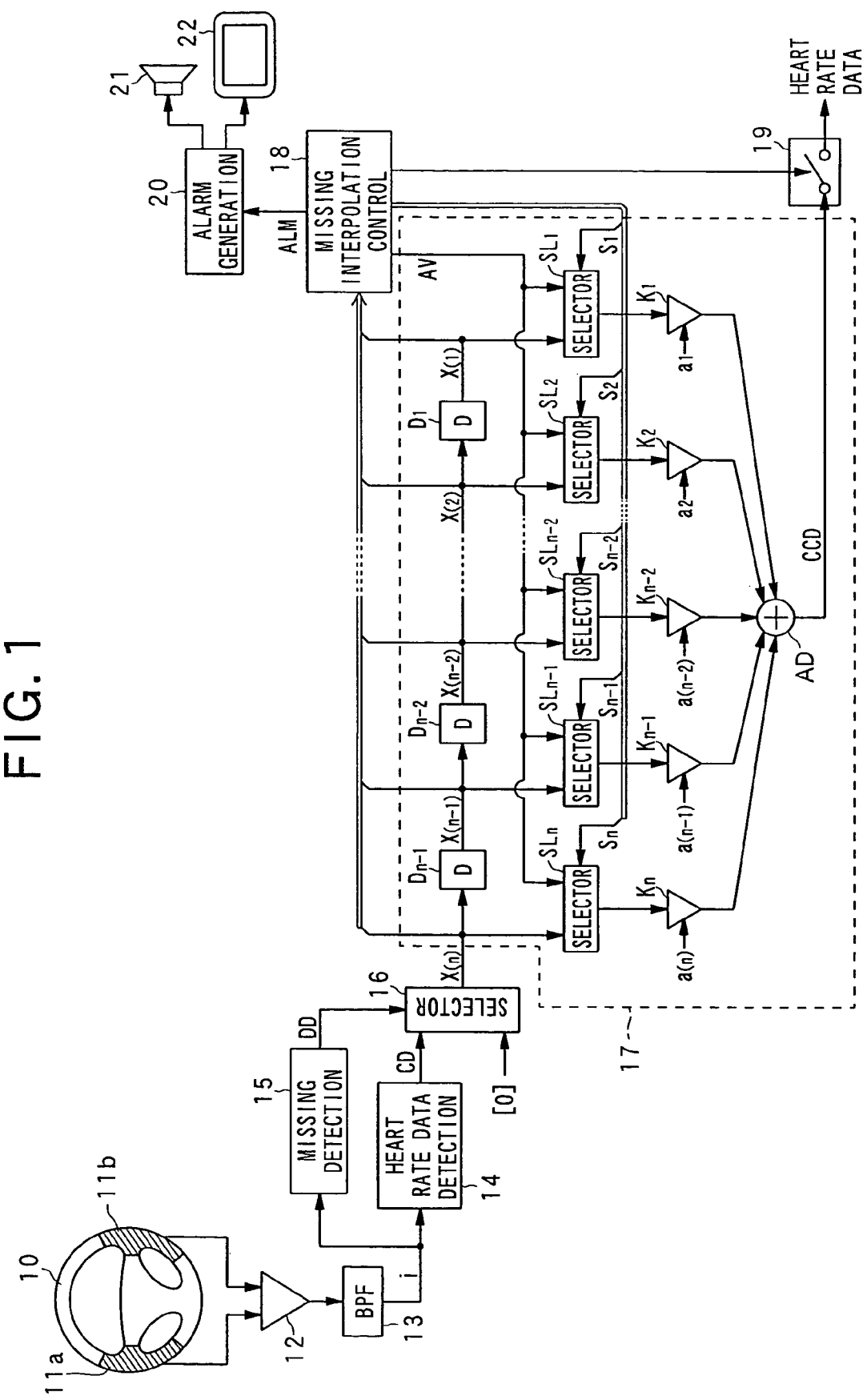
FIG. 1 is a diagram showing a configuration of a heart rate detection apparatus serving as a biological information detection apparatus according to the present invention.

FIG. 1 is a diagram showing a configuration of a heart rate detection apparatus serving as a biological information detection apparatus according to the present invention.

In FIG. 1, a detection electrode 11a for detecting an electric potential of a left hand of a driver and a detection electrode 11b for detecting an electric potential of a right hand are provided on a steering wheel 10 of a vehicle. An amplifier 12 amplifies an electric signal corresponding to a potential difference between the left and right hands of the driver acquired by the detection electrodes 11a and 11b, and supplies a resultant signal to a band pass filter 13. The band pass filter 13 extracts a myocardium pulse signal (an electrocardiogram signal) corresponding to a motion of a myocardium of the driver from the electric signal, and supplies the myocardium pulse signal to a heart rate data detection circuit 14 and a missing detection circuit 15.

The heart rate data detection circuit 14 measures the heart rate per unit time on the basis of the myocardium pulse signal. In addition, the heart rate data detection circuit 14 may measure a 0.15 to 0.4 Hz component of the variation of the pulse interval of the myocardium pulse signal as an RSA (Respiratory Sinus Arrhythmia) value, which represents fluctuation of the pulse interval concerning the respiration variation. The heart rate data detection circuit 14 detects a heart rate data CD, which represents the measured heart rate and RSA value, and supplies it successively to a selector 16 every predetermined repetition period.

If the myocardium pulse signal has noise of at least a predetermined level mixed therein, the missing detection circuit 15 supplies a missing detection signal of a logic level to the selector 16. Otherwise, the missing detection circuit 15 supplies a missing detection signal of a logic level 0 to the selector 16. In other words, if the myocardium pulse signal has noise of at least the predetermined level mixed therein, the missing detection circuit 15 judges that the driver releases a hand from the detection electrode 11a or 11b and consequently the heart rate data CD is missing, and generates the missing detection signal of the logic level 1.

While the missing detection signal of the logic level 0 is being supplied to the selector 16, the selector 16 supplies the heart rate data CD to an FIR (Finite Impulse Response) filter 17 as heart rate data $X_{(n)}$ at an n-th point in time. On the other hand, while the missing detection signal of the logic level 1 is being supplied to the selector 16, the selector 16 supplies "0" to the FIR filter 17 as the heart rate data $X_{(n)}$.

In other words, if the heart rate data CD is correctly acquired, the selector 16 supplies it to the FIR filter 17 as it is, whereas if the heart rate data CD is judged to be missing, the selector 16 supplies "0" to the FIR filter 17.

The FIR filter 17 includes unit delay elements $D_1$ to $D_{n-1}$ connected in series, selectors $SL_1$ to $SL_n$, coefficient multipliers $K_1$ to $K_n$, and an adder AD.

Each of the unit delay elements $D_1$ to $D_{n-1}$ takes in input data at timing of a clock signal having the same repetition period as the above-described predetermined repetition period, and outputs it. In other words, the unit delay element $D_{n-1}$ takes in the input heart rate data $X_{(n)}$ after a delay equivalent to the above-described predetermined repetition period, and outputs it as heart rate data $X_{(n-1)}$ at a point in time (n-1). The unit delay element $D_{n-2}$ takes in the heart rate data $X_{(n-1)}$ after a delay equivalent to the above-described predetermined repetition period, and outputs it as heart rate data $X_{(n-2)}$ at a point in time (n-2). The unit delay element $D_{n-3}$ takes in the heart rate data $X_{(n-2)}$ after a delay equivalent to the above-described predetermined repetition period, and outputs it as heart rate data $X_{(n-3)}$ at a point in time (n-3). In the same way, the unit delay elements $D_{n-4}$ to $D_1$ take in input data after a delay equivalent to the above-described predetermined repetition period, and outputs it as heart rate data $X_{(n-4)}$ at a point in time (n-4) to heart rate data $X_{(1)}$ at a point in time (1) respectively. The heart rate data $X_{(1)}$ to $X_{(n)}$ are supplied to the selectors $SL_1$ to $SL_n$, respectively. The selectors $SL_1$ to $SL_n$ select either the supplied heart rate data X or average heart rate data AV supplied from a missing interpolation control circuit 18, and supplies the selected one to coefficient multipliers $K_1$ to $K_n$, respectively. By the way, the selectors $SL_1$ to $SL_n$ executes the selection described above respectively according to selection signals $S_1$ to $S_n$ supplied from the missing interpolation control circuit 18. For example, if the selection signal $S_1$ is at the logic level 0, the selector $SL_1$ supplies the heart rate data $X_{(1)}$ to the coefficient multiplier $K_1$. On the other hand, if the selection signal S1 is at the logic level 1, the selector $SL_1$ supplies the average heart rate data AV to the coefficient multiplier $K_1$. If the selection signal $S_n$ is at the logic level 0, the selector $SL_n$ supplies the heart rate data $X_{(n)}$ to the coefficient multiplier $K_n$. On the other hand, if the selection signal $S_n$ is at the logic level 1, the selector $SL_n$ supplies the average heart rate data AV to the coefficient multiplier $K_n$.

The coefficient multipliers $K_1$ to $K_n$ supply multiplication results, which are obtained by multiplying data values supplied from the selectors $SL_1$ to $SL_n$ respectively by predetermined coefficients $a_1$ to $a_{(n)}$, to the adder AD. The adder AD finds the sum total of the results of multiplication operations conducted by the coefficient multipliers $K_1$ to $K_n$, and supplies the sum total to a switch 19 as heart rate data CCD. In other words, the coefficient multipliers $K_1$ to $K_n$ and the adder AD conduct weighted addition on the heart rate data X or the average heart rate data AV supplied from the selectors $SL_1$ to $SL_n$, and obtain the heart rate data CCD.

Upon being supplied with an output enable signal from the missing interpolation control circuit 18, the switch 19 assumes the on-state and outputs the heart rate data CCD as heart rate data representing the heart rate of the driver. On the other hand, upon being supplied with an output disable signal from the missing interpolation control circuit 18, the switch 19 assumes the off-state and stops outputting the heart rate data. A navigation apparatus, an acoustic apparatus using mental condition determination, or a sleepiness alarm system (all of which are not illustrated) mounted on a vehicle conducts various mental state determinations including the sleepiness determination of the driver on the basis of heart rate data output from the switch 19.

Incidentally, for example, the detection electrodes 11a and 11b, the amplifier 12, the band pass filter 13, and the heart rate data detection circuit 14 according to this embodiment serve as a sensor according to the present invention; the missing detection circuit 15 according to this embodiment serves as a missing detection device according to the present invention; the unit delay elements $D_1$ to $D_{n-1}$ according to this embodiment serve as a storage device according to the present invention; the missing interpolation control circuit 18 according to this embodiment serves as an average calculation device and a missing interpolation device according to the present invention; the selectors $SL_1$ to $SL_n$, the coefficient multipliers $K_1$ to $K_n$, and the adder AD according to this embodiment serve as a weighted addition device according to the present invention; and the missing interpolation control circuit 18 and the switch 19 according to this embodiment serve as a device which stops outputting the biological signal according to the present invention.

Figure 2:
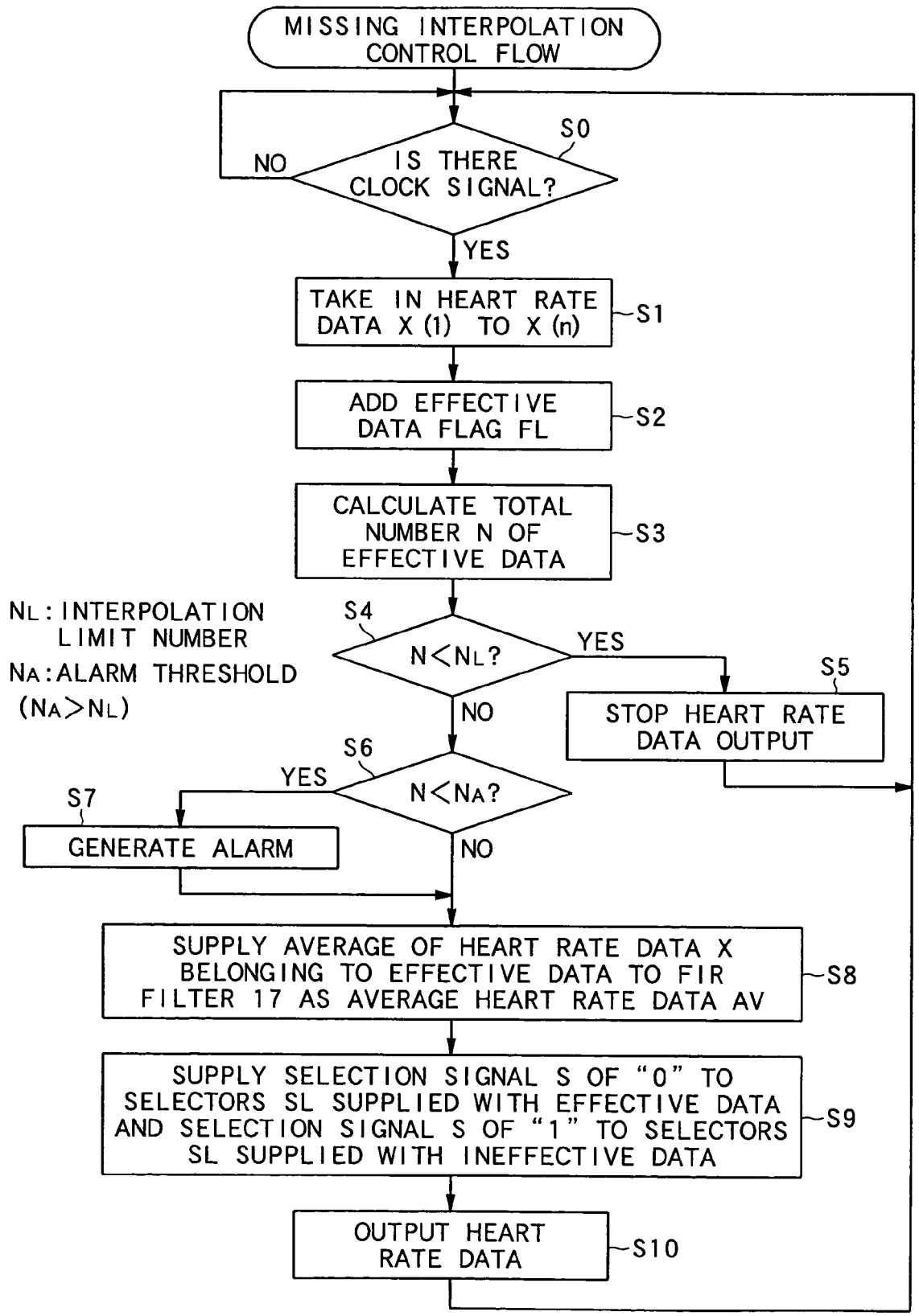
FIG. 2 is a diagram showing a missing interpolation control flow executed by a missing interpolation control circuit 18 shown in FIG. 1.

In accordance with a missing interpolation control flow as shown in FIG. 2, the missing interpolation control circuit 18 executes control on the FIR filter 17, the switch 19 and an alarm generation circuit 20.

Also, for example, the alarm generation circuit 20 according to this embodiment serves as an alarm device according to the present invention.

With reference to FIG. 2, first, the missing interpolation control circuit 18 repetitively executes a determination whether the rising edge of the clock signal has been detected, until a determination that the rising edge of the clock signal has been detected is obtained (step S0). Upon determining at the step S0 that the rising edge of the clock signal has been detected, the missing interpolation control circuit 18 stores the heart rate data $X_{(1)}$ to $X_{(n)}$ supplied from the FIR filter 17 in an internal memory (not illustrated) (step S1). Subsequently, the missing interpolation control circuit 18 stores an effective data flag FL as shown in FIG. 3 in the internal memory in association with each of heart rate data X which are included in the heart rate data $X_{(1)}$ to $X_{(n)}$ and which are different from 0 in value (step S2). At this time, heart rate data X provided with the effective data flag FL indicates effective data, whereas heart rate data X which is not provided with the effective data flag FL indicates ineffective data acquired at the time of missing.

Subsequently, the missing interpolation control circuit 18 finds the total number of effective data flags FL added so as to be associated with the heart rate data $X_{(1)}$ to $X_{(n)}$ as shown in FIG. 3, and stores the total number as the total number N of effective data (step S3). Subsequently, the missing interpolation control circuit 18 determines whether the total number N of effective data is less than an interpolation limit number $N_L$ which can be interpolated by the FIR filter 17 (step S4). If the total number N of effective data is determined at the step S4 to be less than the interpolation limit number $N_L$, the missing interpolation control circuit 18 supplies the output disable signal to the switch 19 (step S5). By executing the step S5, the switch 19 assumes the off-state and stops outputting the heart rate data. In other words, if the number N of effective data included in the heart rate data $X_{(1)}$ to $X_{(n)}$ respectively corresponding to the first point in time to the n-th point in time is less than the interpolation limit number $N_L$, then interpolation for the missing section cannot be conducted, and consequently outputting the heart rate data is stopped.

After execution of the step S5, the missing interpolation control circuit 18 returns to execution of the step S0 and repetitively executes the operation described above.

On the other hand, if the total number N of effective data is determined at the step S4 not to be less than the interpolation limit number $N_L$, then the missing interpolation control circuit 18 determines whether or not the total number N of effective data is less than an alarm threshold $N_A$, which is greater than the interpolation limit number $N_L$ by a predetermined number (step S6). If the total number N of effective data is determined at the step S6 to be less than the alarm threshold $N_A$, then the missing interpolation control circuit 18 supplies an alarm signal ALM to the alarm generation circuit 20 (step S7). By executing the step S7, the alarm generation circuit 20 supplies an audio signal and a video signal corresponding to a guide announcement, which urges the driver to bring one hand or both hands respectively into positive contact with the detection electrodes 11, to a speaker 21 and a display apparatus 22, respectively. In other words, if the number N of effective data included in the heart rate data $X_{(1)}$ to $X_{(n)}$ respectively corresponding to the first point in time to the n-th point in time approaches the interpolation limit number $N_L$, the alarm is given to the driver before the number of effective data becomes less than the interpolation limit number $N_L$. By the way, the generation of the alarm at the step S7 is not executed each time the total number N of effective data is determined to be less than the alarm threshold $N_A$. For example, if the total number of times the total number N of effective data is determined to be less than the alarm threshold $N_A$ has exceeded six, the alarm is generated at the step S7.

After the execution of the step S7, or when the total number N of effective data is determined at the step S6 not to be less than the alarm threshold $N_A$, the missing interpolation control circuit 18 conducts the following operation. The missing interpolation control circuit 18 calculates an average value of heart rate data included in the heart rate data $X_{(1)}$ to $X_{(n)}$ stored in the internal memory and provided with the effective data flag FL, and supplies the average value to the selectors $SL_1$ to $SL_n$ in the FIR filter 17 respectively as average heart rate data AV (step S8). Subsequently, the missing interpolation control circuit 18 supplies a selection signal S of a logic level 0 to each of selectors SL supplied with heart rate data X provided with the effective data flag FL as shown in FIG. 3, and supplies a selection signal S of a logic level 1 to each of selectors SL supplied with heart rate data X which are not provided with the effective data flag FL (step S9). For example, if the heart rate data $X_{(1)}$ and $X_{(5)}$ to $X_{(n)}$ are provided with the effective data flag FL as shown in FIG. 3, the missing interpolation control circuit 18 supplies a selection signal S of a logic level 0 to the selectors $SL_1$ and $SL_5$ to $SL_n$, and supplies a selection signal S of a logic level 1 to the selectors $SL_2$ to $SL_4$. As a result of the execution at the step S9, each of selectors SL supplied with a selection signal S of a logic level 0 supplies heart rate data X to a corresponding coefficient multiplier K, whereas each of selectors SL supplied with a selection signal S of a logic level 1 supplies the average heart rate data AV instead of the heart rate data X to a corresponding coefficient multiplier K. In other words, if heart rate data X is provided with the effective data flag FL, the heart rate data X is supplied to the coefficient multiplier K as it is. As for heart rate data X which is not provided with the effective data flag FL, i.e., heart rate data X determined to be so-called ineffective data, however, the average heart rate data AV, which is the average value of the heart rate data determined to be effective data, is supplied to the coefficient multiplier K, instead of the heart rate data X. In other words, if the driver releases one hand or both hands from the detection electrodes 11 and consequently a myocardium pulse signal (an electrocardiogram signal) output from the band pass filter 13 is missing and the heart rate data X has become ineffective data, then interpolation using the average heart rate data AV is conducted.

After the execution at the step S9, the missing interpolation control circuit 18 supplies the output enable signal to the switch 19 (step S10). Thereafter, the missing interpolation control circuit 18 returns to the execution of the step S0, and executes the above-described operation repetitively. As a result, a result obtained by conducting the weighted addition on heart rate data X at points in time which are included in n consecutive points in time and which are not included in the missing section and on the average heart rate data AV at points in time which are included in the missing section is generated as heart rate data CCD representing the heart rate of the driver.

For example, if all of the heart rate data $X_{(1)}$ to $X_{(n)}$ are effective data, heart rate data represented as below is output.

$$CCD = a_1 \cdot X_{(1)} + a_2 \cdot X_{(2)} + a_3 \cdot X_{(3)} + a_4 \cdot X_{(4)} + a_5 \cdot X_{(5)} +, \ldots, + a_{n-1} \cdot X_{(n-1)} + a_n \cdot X_{(n)}$$

On the other hand, if the driver releases one hand or both hands from the detection electrodes 11 and consequently a myocardium pulse signal (an electrocardiogram signal) output from the band pass filter 13 is missing, interpolation in the missing section is conducted by using an average value of heart rate data already acquired until then. Therefore, it becomes possible to continuously output the heart rate data CCD.

Figure 4:
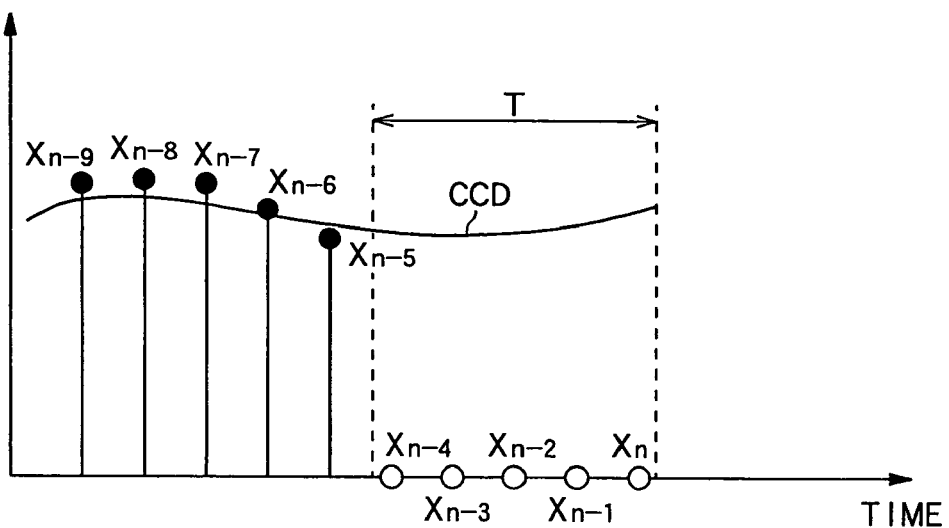
FIG. 4 is a diagram showing an example of operation according to the present invention.

For example, even if a myocardium pulse signal output from the band pass filter 13 is missing and consequently heart rate data CD to be generated in the heart rate data generation circuit 14 is missing over a missing section T as shown in FIG. 4 and the heart rate data $X_{(n-4)}$ to $X_{(n)}$ (represented by white circles) become ineffective data, interpolation is conducted over the section by using an average value (AV) of effective data (represented by black circles) included in heart rate data already acquired. For example, at a point n in time in the missing section T as shown in FIG. 4, heart rate data represented as below is output.

$$CCD = a_1 \cdot X_{(1)} + a_2 \cdot X_{(2)} + a_3 \cdot X_{(3)} + a_4 \cdot X_{(4)} + a_5 \cdot X_{(5)} +, \ldots, + AV \cdot X_{(n-4)} + AV \cdot X_{(n-3)} + AV \cdot X_{(n-2)} + AV \cdot X_{(n-1)} + AV \cdot X_{(n)}$$

Even over the missing section T, therefore, it becomes possible to continuously output the heart rate data CCD as represented by a solid line in FIG. 4.

In the above-described embodiment, the heart rate detection apparatus which detects heart rate as biological information of a driver has been described. However, biological information to be detected is not limited to the heart rate, but the present invention can be applied to various biological information detection apparatuses for pulsebeat, respiration, temperature, skin resistance, blood pressure, brain waves, or the like.

In the foregoing description of the embodiment, each of the bandpass filter 13, the heart rate data detection circuit 14, the missing detection circuit 15, the selector 16, the FIR filter 17, the missing interpolation control circuit 18 and the switch 19 has a hardware configuration. However, these functions may be implemented by software.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2003-132743 filed on May 12, 2003 including the specification, claims, drawings and summary is incorporated herein by reference in its entirety.

What is claimed is:

1. A biological information detection apparatus which detects biological information of a human body, the biological information detection apparatus comprising:

a sensor which detects an electric signal corresponding to the biological information from the human body as a biological signal;

a missing detection device which detects a missing section of the biological signal;

a storage device which stores the biological signal at each of n (where n is a natural number) consecutive points in time;

an average calculation device which calculates an average value of the biological signal at points in time which are included in the n points in time and which are not included in the missing section;

a weighted addition device which outputs a result obtained by conducting weighted addition on the biological signal at the n points in time, as a final biological signal; and a missing interpolation device which, in conducting the weighted addition, changes the biological signal at each of the points in time included in the missing section to the average value.

2. The biological information detection apparatus according to claim 1, wherein the storage device changes the biological signal at each of the points in time included in the missing section to a predetermined value and stores the predetermined value.

3. The biological information detection apparatus according to claim 1, wherein the weighted addition device comprises a device which stops outputting the biological signal when a total number of points in time which are included in the n points in time and which are not included in the missing section is less than a first predetermined number.

4. The biological information detection apparatus according to claim 3, further comprising an alarm device which gives an alarm when the total number of points in time which are included in the n points in time and which are not included in the missing section is less than a second predetermined number which is greater than the first predetermined number.

* * * * *